United States Patent [19]

Suzuki

[11] Patent Number: 4,966,157
[45] Date of Patent: Oct. 30, 1990

[54] ELECTROCARDIOGRAPH OPERABLE TO FORM UPDATED SEQUENTIAL SERIES OF CARDIOGRAPHIC SIGNALS

[75] Inventor: Takashi Suzuki, Kyoto, Japan

[73] Assignee: Sharp Kabushiki Kaisha, Osaka, Japan

[21] Appl. No.: 324,082

[22] Filed: Mar. 16, 1989

[30] Foreign Application Priority Data

Mar. 17, 1988 [JP] Japan ................................ 63-65246

[51] Int. Cl.$^5$ .............................................. A61B 5/04
[52] U.S. Cl. .................................................. 128/696
[58] Field of Search ............... 128/696, 695, 699, 702, 128/703, 704, 705, 706, 708, 710, 711

[56] References Cited

U.S. PATENT DOCUMENTS

| 3,835,455 | 9/1974 | Abbenante | 340/172.5 |
|---|---|---|---|
| 4,183,354 | 1/1980 | Sibley et al. | 128/711 |
| 4,457,315 | 7/1984 | Bennish | 128/711 |
| 4,653,022 | 3/1987 | Koro | 128/696 |
| 4,696,306 | 9/1987 | Shiozaki | 128/696 |
| 4,754,762 | 7/1988 | Stuchl | 128/696 |

FOREIGN PATENT DOCUMENTS 2034046 9/1979 United Kingdom ................ 128/711

OTHER PUBLICATIONS

"Design, Implementation and Evaluation of a Microcomputer-based Portable Arrhythmia Monitor"; N.V. Thakor et al.; Mar. 22, 1984.

Primary Examiner—Francis Jaworski
Assistant Examiner—George Manuel

[57] ABSTRACT

An electrocardiograph which includes a detecting circuit for detecting a cardiographic signal from a living body; a storage circuit for storing the cardiographic signal from the detecting circuit; a storage control circuit capable of performing a storage control operation in such a way as to sequentially and continuously store a new cardiographic signal in the storage circuit for the formation of cardiographic data and as to successively erase old cardiographic data which are stored in the storage circuit; and a cardiographic data hold commanding circuit operable in response to a cardiographic data hold commanding signal to command the retaining of cardiographic data in the storage circuit.

17 Claims, 2 Drawing Sheets

ELECTROCARDIOGRAPH OPERABLE TO FORM UPDATED SEQUENTIAL SERIES OF CARDIOGRAPHIC SIGNALS

BACKGROUND OF THE INVENTION

Field of the Invention

The present invention relates to an electrocardiograph capable of providing electrocardiographic data.

Description of the Prior Art

As an electrocardiograph, Holter electrocardiograph is well known. Holter electrocardiograph is so designed as to monitor a cardiographic signal, detected from a living body, continuously for a maximum of 24 hours and record electrocardiographic data on an analog tape. A patient whose cardiographic data are required to be monitored may be a patient suffering from angina pectoris decubitus, i.e, the patient who tends to have a heart attack for example, once a week. The patient suffering from this disease is generally required to provide cardiographic data from time to time and, therefore, with Holter electrocardiograph, a roll of recording tape has to be supplemented each day while a number of rolls of recording tape has to be stocked for the time of use.

Apart from Holter electrocardiograph, a handy electrocardiograph is also well known which can provide cardiographic data when the patient operates it in the event of a heart attack. While this known handy electrocardiograph is effective to provide useful cardiographic data at the time of occurrence of the heart attack, it cannot provide abnormal cardiographic data which shows the occurrence of a heart attack during, for example, sleeping.

SUMMARY OF THE INVENTION

Therefore, the present invention has been devised in light of the problems inherent in the prior art electrocardiographs and is intended to provide an improved electrocardiograph capable of providing required cardiographic data assuredly and without difficulty.

In order to accomplish the above described object, the present invention provides an electrocardiograph which comprises a detecting means for detecting a cardiographic signal from a living body, a storage means for storing the cardiographic signal from the detecting means, a storage control means capable of performing a storage control operation in such a way as to sequentially and continuously store a new cardiographic signal in the storage means for the formation of cardiographic data and as to successively erase old cardiographic data which are stored in the storage means, and a cardiographic data hold commanding means operable in response to a cardiographic data hold commanding signal to command the retaining of the cardiographic data in the storage means.

According to the present invention, the cardiographic data are updated and stored in a predetermined quantity with passage of time in the storage means by the storage control means and the cardiographic data in the storage means can be retained by a hold command issued from the hold commanding means.

BRIEF DESCRIPTION OF THE DRAWINGS

These and other objects and features of the present invention will become clear from the following description taken in conjunction with a preferred embodiment thereof with reference to the accompanying drawings which are given by way of illustration only, and thus are not limitative of the present invention, and wherein.

DETAILED DESCRIPTION OF THE EMBODIMENT

Figure 1:
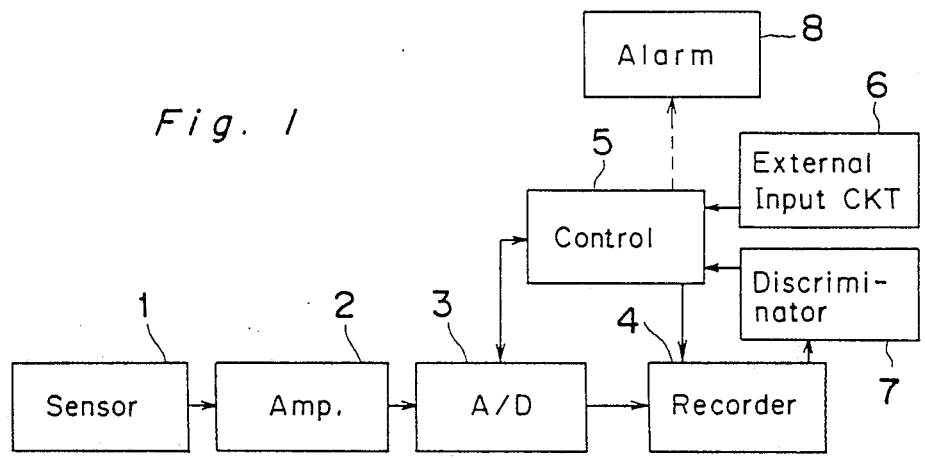
FIG. 1 is a block circuit diagram showing the overall structure of an electrocardiograph according to the present invention.

Referring first to FIG. 1, reference numeral 1 represents a sensor (a detecting means); reference numeral 2 represents an amplifier circuit; reference numeral 3 represents an analog-to-digital converter (A/D); reference numeral 4 represents a recording unit (a storage means); and reference numeral 5 represents a control circuit (a storage control means, a hold commanding means). A cardiographic signal provided from the sensor 1 which is held in contact with a living body is amplified by the amplifier circuit 2 and is then converted into a digital signal by the A/D converter 3 which performs an A/D conversion in response to an A/D conversion command supplied from the control circuit 5, which digital signal is stored in the recording unit 4 from time to time.

In the recording unit 4, on the basis of a storage control signal supplied from the control circuit 5, a new digital cardiographic signal is stored so as to form cardiographic data sequentially and continuously, and the stored cardiographic data are erased in order from older ones to newer ones while a predetermined quantity of cardiographic data are successively updated and stored.

Reference numeral 6 represents an external input unit such as a keyboard and reference numeral 7 represents a discriminating circuit. A start signal and a first hold commanding signal, as will be described later, are supplied as input from the external input unit 6 to the control circuit 5. The discriminating circuit 7 determines the presence or absence of an abnormality in the new digital cardiographic signal which is being stored in the recording unit 4 and generates a second hold commanding signal (an abnormality signal) to the control circuit 5 in the event of the presence of abnormality.

Figure 6:
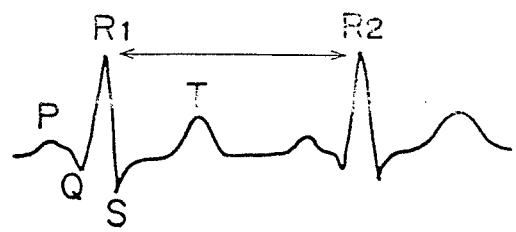
FIG. 6 is a fragmentary cardiogram used to illustrate the determination of the presence or absence of an abnormality.

The determination of the presence or absence of an abnormality performed by the discriminating circuit 7 is carried out in such a manner that, assuming that the cardiographic signal obtained represents, for example, such a waveform as shown in FIG. 6, if the heart rate ($1/R_1-R_2$ hour) is within the range of 50 to 100 beats per minute, the absence of abnormality can be determined, but if the heart rate is out of the above range, the presence of abnormality such as bradycardia or tachycardia can be determined.

The first and second hold commanding signals referred to above are cardiographic data hold commanding signals of the present invention and are applied to the recording unit 4 through the control circuit 5. The recording unit 4 is adapted to retain all of the stored contents being updated and stored in response to the first hold commanding signal and a latter half of the stored contents in response to the second hold commanding signal.

Figure 2:
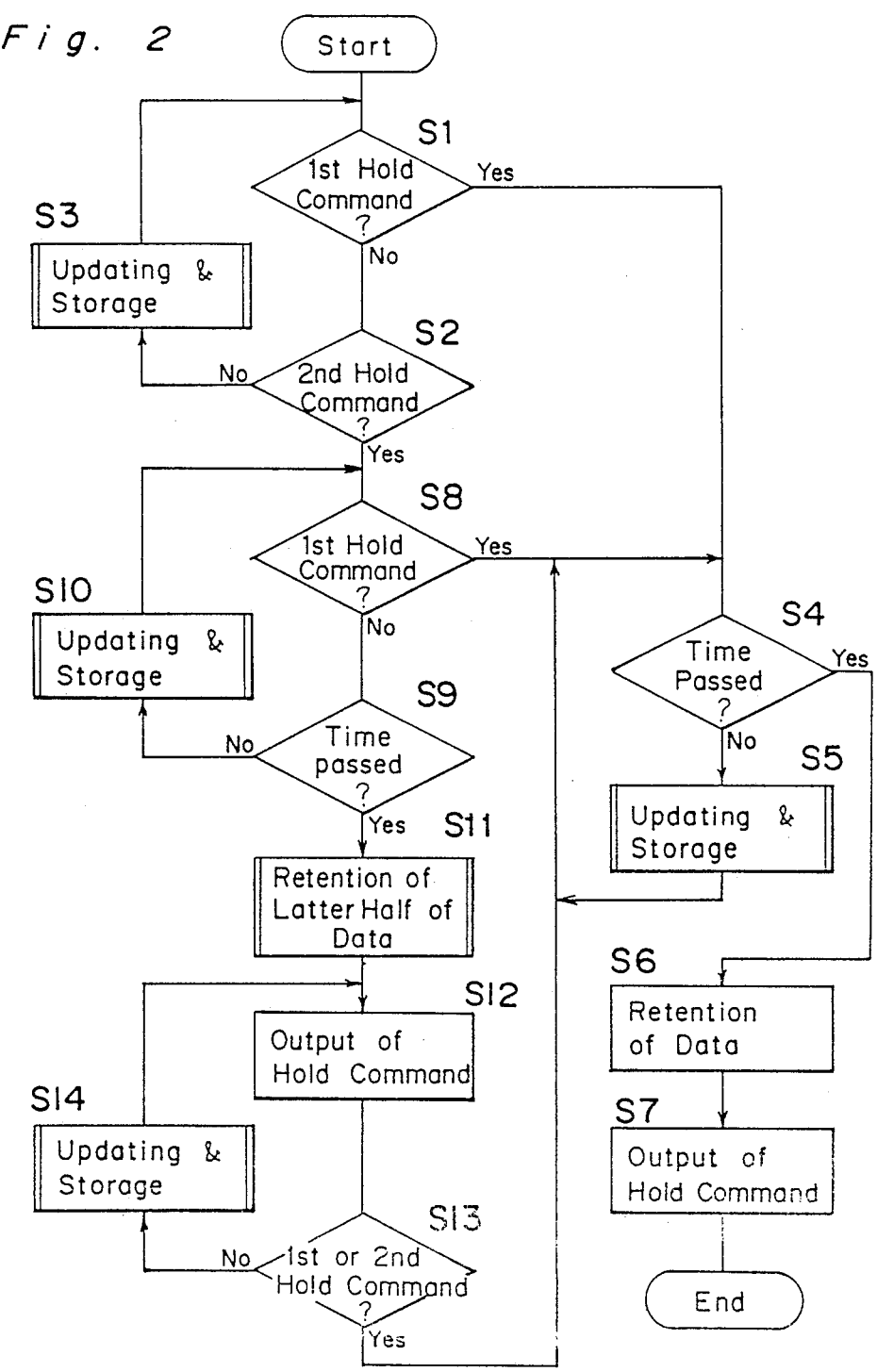
FIG. 2 is a flow chart showing the sequence of operation of the electrocardiograph shown in FIG. 1.

The operation of the above described embodiment will now be described with reference to the flow chart of FIG. 2 showing the sequence of operation of the control circuit 5.

The operation starts when an electric power source switch is turned on, and a decision is made at step S1 and then at step S2 to determine the presence or absence of the first hold commanding signal and then that of the second hold commanding signal. Should the first and second hold commanding signals not be present, the A/D conversion commanding signal and the storage control signal are supplied from the control circuit 5 to the A/D converter 3 and the recording unit 4, respectively, causing the recording unit 4 to sequentially and continuously store the digital cardiographic signal supplied from the A/D converter 3 at step S3.

Figure 3:
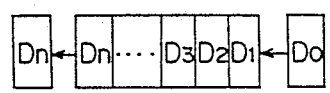
FIGS. 3 to 5 are explanatory diagrams used to explain the operation of a recording unit.

At the time of initiation, the recording unit 4 stores nothing and is in an all cleared state and, each time the flow from step S1 back to step S1 via steps S2 and S3 is repeated, the storage amount thereof is increased. After storage areas are filled, as shown in FIG. 3, the oldest data portion Dn is erased each time a new digital signal Do is applied, that is, the cardiographic data stored are updated at step S3 with passage of time.

The first hold commanding signal referred to above is applied when the patient suffering from the attack inputs it by manipulating the external input unit 6, whereas the second hold commanding signal is applied from the discriminating circuit 7 in the event of occurrence of an abnormality in the cardiographic signal.

Should the result of the decision at step S1 indicate the presence of the first hold commanding signal, the length of time passed subsequent to the generation of the first hold commanding signal is counted at step S4. Since the counted length of time has not yet exceeded a preset value immediately after the generation of the first hold commanding signal, the updating and storage operation is carried out at step S5 in a manner similar to that at step S3 and the program flow then returns to step S4. The updating and storage operation at step S5 is repeated before the counted length of time exceeds the preset value and, thereafter, i.e., after the passage of the preset length of time, the program flow proceeds to step S6 at which the whole of the cardiographic data $D_1$ to $D_n$ then stored are retained with the updating interrupted, with the operation subsequently terminating when the hold command is outputted from the control circuit 5.

As hereinabove described, since subsequent to the generation of the first hold commanding signal at step S1, the updating and storage operation at step S5 is repeated a plurality of times before the preset time passes, the cardiographic signal available at the time of generation of the first hold commanding signal occupies a position intermediate of the cardiographic data retained, that is, the cardiographic data including those portions before and after the outputting of the first hold commanding signal are retained in the recording unit 4.

The hold signal outputted at step S7 is used as a warning signal for a retention alarm 8 which may be optionally used, and the retention alarm 8 if used may be a warning ring capable of generating warning sounds, a display providing a visual warning display, a warning lamp or a combination thereof, provided that owing to the indication provided by the retention alarm 8 the hold operation can be confirmed from the outside on a real-time basis.

Figure 4:

In the event that the result of decision at step S2 indicates that an abnormality is found in the cardiographic signal and that the second hold commanding signal has been generated, a decision is made at step S8 to determine the presence or absence of the first hold commanding signal. It is determined that the first hold commanding signal is not present, in a manner similar to the repeated flow from step S4 back to step S4 via step S5, the program flow is repeated from step S9 back to step S9 via step S10, followed by the retention at step S11 of a latter half (data $D_{m+1}$ to $D_n$) of the cardiographic data to be stored as shown in FIG. 4 with the abnormal cardiographic signal retained at the intermediate position. Thereafter, the hold signal therefor is outputted at step S12 in a manner similar to that at step S7.

From step S8, the program flow proceeds to step S4, and the flow from any one of steps S2 and S10 to step S8 is caused to occur so that, even after the presence of the second hold commanding signal has been once determined, priority can be given to a corresponding operation in relation to the first hold commanding signal in the event of the presence of the first hold commanding signal.

Figure 5:
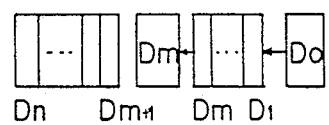

After the generation of the hold command at step S12, a decision is made at step S13 to determine the presence or absence of the first or second hold commanding signal. In the event of the absence of both of the first and second hold commanding signals, as shown in FIG. 5, the updating and storage operation of the remaining first half (data $D_o$ to $D_m$) of the cardiographic data is carried out at step S14. Should the presence of the hold command be found at step S13, the program flow proceeds to step S4, and the holding operation at step S6 in that case is carried out in the first half of the data wherefore both of the first half and latter half of the cardiographic data can be retained in the recording unit 4.

The retained data so obtained can be displayed by a display unit, integrated with the electrocardiograph or connected therewith, in response to a manipulation done to effect the display.

In the foregoing embodiment, the number of divisible memory areas in the recording unit 4 has been shown as two, but it may be possible to increase it to a number greater than two so that the number of times of retention resulting from the first or second hold commanding signal can be increased thereby enabling a plurality of retained data to be obtained for each cycle of operation. Also, the recording unit 4 may be so constructed that some other data useful for the diagnosis of the cardiographic data such as the time of detection, the heart rate trend, ST trend, etc., can be recorded simultaneously.

Also, in the foregoing embodiment of the present invention, arrangement has been made that the retaining operation can be performed by the first or second hold commanding signal. However, it is possible to make the retaining operation to be performed relying only on a hold commanding signal corresponding to the second hold commanding signal and, in such case, arrangement may be made so that the retained data can be cancelled by depressing a cancel key which may be depressed by the patient when no attack occurred while data can be obtained in the event of the occurrence of the attack.

Since the present invention is so constructed as hereinabove fully described, that is, since the cardiographic data can be updated and stored in the storage means with passage of time and retained in response to the hold command issued from the hold commanding means, the electrocardiograph according to the present invention is effective in that the necessary cardiographic data can be easily obtained within the framework of the limited storage capacity.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An electrocardiograph comprising:
   detecting means for detecting cardiographic signals from a living body;
   storage means for storing a sequential series of said detected cardiographic signals;
   storage control means for performing a storage control operation to suquentially store a newly detected cardiographic signal as a most recent detected cardiographic signal in said sequential series of said detected cardiographic signals and to delete the least recent detected cardiographic signal of said sequential series of said detected cardiographic signals to form an updated sequential series of said detected cardiographic signals; and
   cardiographic data hold commanding means operable in response to a data hold commanding signal to command the retaining of an updated sequential series of said detected cardiographic signals in said storage means.

2. The electrocardiograph as claimed in claim 1 wherein said cardiographic data hold commanding signal comprises a first hold commanding signal generated by a user in the event of occurrence of a heart attack and a second hold commanding signal generated by abnormality detecting means in the event of the presence of an abnormality in a detected cardiographic signal.

3. The electrocardiograph as claimed in claim 1, wherein said cardiographic data hold commanding signal comprises a first hold commanding signal generated by a user in the event of occurrence of a heart attack and a second hold commanding signal generated by abnormality detecting means in the event of the presence of an abnormality in a detected cardiographic signal, and wherein, in the event that said first and second hold commanding signals are simultaneously asserted, a holding operation based on said first hold commanding signal is carried out prior to a holding operation based on said second hold commanding signal.

4. The electrocardiograph of claim 1 wherein said cardiographic data hold commanding means is operable to command the continual formation of updated sequential series of said detected cardiographic signals for a predetermined time in response to said data hold commanding signal and to command the retaining of an updated sequential series of said detected cardiographic signals in said storage means after lapsing of said predetermined time.

5. A method of operating an electrocardiograph which includes cardiographic detecting means, storage means, control means and cardiographic data hold commanding means comprising the steps of:
   (a) determining, in the control means, if a first hold commanding signal from the cardiographic data hold commanding means is present;
   (b) determining, in the control means, if a second hold commanding signal from the cardiographic data hold commanding means is present; and
   (c) sequentially storing detected cardiographic signals output from the cardiographic detecting means in the storage means and continuously repeating steps (a) and (b) to form a sequential series of detected cardiographic signals if said first and second data hold command signals are not present.

6. The method of operating an electrocardiograph of claim 5 wherein once the storage means is full, a newly detected cardiographic signal is stored as a most recent detected cardiographic signal and the least recent detected cardiographic signal is deleted to form an updated sequential series of said detected cardiographic signals.

7. The method of operating an electrocardiograph of claim 6 further comprising the steps of:
   (d) continuously forming updated sequential series of said detected cardiographic signals for a predetermined time after the control means has determined said first hold commanding signal is present; and
   (e) storing an updated sequential series of said detected cardiographic signals after said predetermined time has elapsed.

8. The method of operating an electrocardiograph of claim 7 further comprising the step of:
   (f) generating an alarm to indicate said storing of said updated sequential series of said detected cardiographic signals of step (e) and termination of said operation.

9. The method of operating an electrocardiograph of claim 6 further comprising the steps of:
   (d) determining, in the control means, if said first hold commanding signal is present once the control means has determined that said second hold commanding signal is present;
   (e) continuously forming updated sequential series of said detected cardiographic signals for a first predetermined time if the control means had determined said first hold commanding signal is not present; and
   (f) storing a latter portion of an updated sequential series of said detected cardiographic signals in the storage means after said first predetermined time has elapsed.

10. The method of operating an electrocardiograph of claim 9 further comprising the step of:
    (g) generating an alarm to indicate said storing of said latter portion of an updated sequential series of said detected cardiographic signals.

11. The method of operating an electrocardiograph of claim 10 further comprising the steps of:
    (h) determining, in the control means, if said first and second hold commanding signals are present once said alarm has been generated in step (g); and
    (i) continuously forming updated sequential series of said detected cardiographic signals of an initial portion of said updated sequential series of detected cardiographic signals of step if said first and second hold commanding signals are not present.

12. The method of operating an electrocardiograph of claim 11 further comprising the steps of:
    (j) continuously forming updated sequential series of said detected cardiographic signals of said initial portion of said updated sequential series of detected cardiographic signals of step (i) for a second predetermined time if the control means has determined said first or second hold commanding signals are present; and (k) storing an updated sequential series of said detected cardiographic signals of said initial portion of said updated sequential series of detected cardiographic signals after said second predetermined time has elapsed.

13. The method of operating an electrocardiograph of claim 12 further comprising the step of:

(l) generating an alarm to indicate said storing of said updated sequential series of said detected cardiographic signals of said initial portion of said updated sequential series of cardiographic signals and termination of said operation.

14. The method of operating an electrocardiograph of claim 9 further comprising the steps of:

(g) continuously forming updated sequential series of said detected cardiographic signals for a second predetermined time after the control means has determined that said first hold commanding signal is present after the control means has determined in step (d) that said second hold commanding signal is present; and (h) storing an updated sequential series of said detected cardiographic signals after said second predetermined time has elapsed.

15. The method of operating an electrocardiograph of claim 14 further comprising the step of:

(i) generating an alarm to indicate said storing of said updated sequential series of said detected cardiographic signals of step (h) and termination of said operation.

16. An electrocardiograph comprising:

detecting means for detecting cardiographic signals from a living body;

storage means for storing said cardiographic signals;

storage control means for performing a storage control operation to sequentially and continuously store new cardiographic signals in said storage means and to successively delete old cardiographic signals from said storage means to form updated sequential series of cardiographic signals; and cardiographic data hold commanding means operable in response to a cardiographic hold commanding signal to command the retaining of an updated sequential series of cardiographic signals in said storage means after a predetermined time.

17. A method of operating an electrocardiograph comprising the steps of:

detecting cardiographic signals from a living body with cardiographic detecting means;

sequentially and continuously storing new cardiographic signals in a storage means and successively deleting old cardiographic signals from said storage means to form updated sequential series of cardiographic signals; and retaining an updated sequential series of cardiographic signals in said storage means a predetermined time after receipt of a cardiographic hold commanding signal from a cardiographic hold command means.

* * * * *